(12) United States Patent  (10) Patent No.: US 7,479,117 B2
Zadow  (45) Date of Patent: Jan. 20, 2009

(54) SINGLE USE BIOPSY DEVICE AND METHOD

(75) Inventor: Paul Andrew Zadow, Allenby Gardens (AU)

(73) Assignee: AUS Systems Pty. Ltd., Allenby Gardens, SA (AU)

( * ) Notice: Subject to any disclaimer, the term of this patent is extended or adjusted under 35 U.S.C. 154(b) by 14 days.

(21) Appl. No.: 11/571,429

(22) PCT Filed: Jul. 8, 2005

(86) PCT No.: PCT/AU2005/001011

§ 371 (c)(1),
(2), (4) Date: Jan. 5, 2007

(87) PCT Pub. No.: WO2006/005121

PCT Pub. Date: Jan. 19, 2006

(65) Prior Publication Data

US 2007/0239065 A1  Oct. 11, 2007

(30) Foreign Application Priority Data

Jul. 9, 2004 (AU) .............................. 2004903750

(51) Int. Cl.
*A61B 10/02* (2006.01)
(52) U.S. Cl. ....................... 600/567; 604/110
(58) Field of Classification Search ................. 600/567; 604/110

See application file for complete search history.

(56) References Cited

U.S. PATENT DOCUMENTS

| 4,826,490 | A | * | 5/1989 | Byrne et al. | ................. 604/198 |
| 5,341,816 | A | * | 8/1994 | Allen | ......................... 600/567 |
| 5,873,886 | A | * | 2/1999 | Larsen et al. | ................ 606/180 |
| 6,346,085 | B1 | * | 2/2002 | Schiffman | .................. 600/565 |
| 6,516,947 | B1 | * | 2/2003 | Van Dyke et al. | ........... 206/361 |
| 6,638,235 | B2 | * | 10/2003 | Miller et al. | ................ 600/566 |
| 2002/0198467 | A1 | | 12/2002 | Finer | |
| 2004/0267157 | A1 | | 12/2004 | Miller et al. | |

FOREIGN PATENT DOCUMENTS

DE  20021405 U1  3/2001

* cited by examiner

*Primary Examiner*—Max Hindenburg
*Assistant Examiner*—Renee Danega
(74) *Attorney, Agent, or Firm*—William J. Sapone; Coleman Sudol Sapone P.C.

(57) ABSTRACT

A single use biopsy device (100) is disclosed. The device (100) includes a receptacle (102) having a port (104) for allowing tissue from a biopsy site to protrude into the receptacle (102) and a cutter (106) that is supported in the receptacle (102) and arranged so that when tissue from a biopsy site protrudes into the receptacle (102) through the port (104) the cutter (106) is movable to sever the tissue so as to obtain a biopsy sample. A stop (108) arrests the cutter (106) after the cutter (106) has severed the tissue. The arresting of the cutter by the stop (108) prevents reuse of the device (100). A method of obtaining a biopsy sample from a biopsy site using the biopsy device (100) is also disclosed.

39 Claims, 10 Drawing Sheets

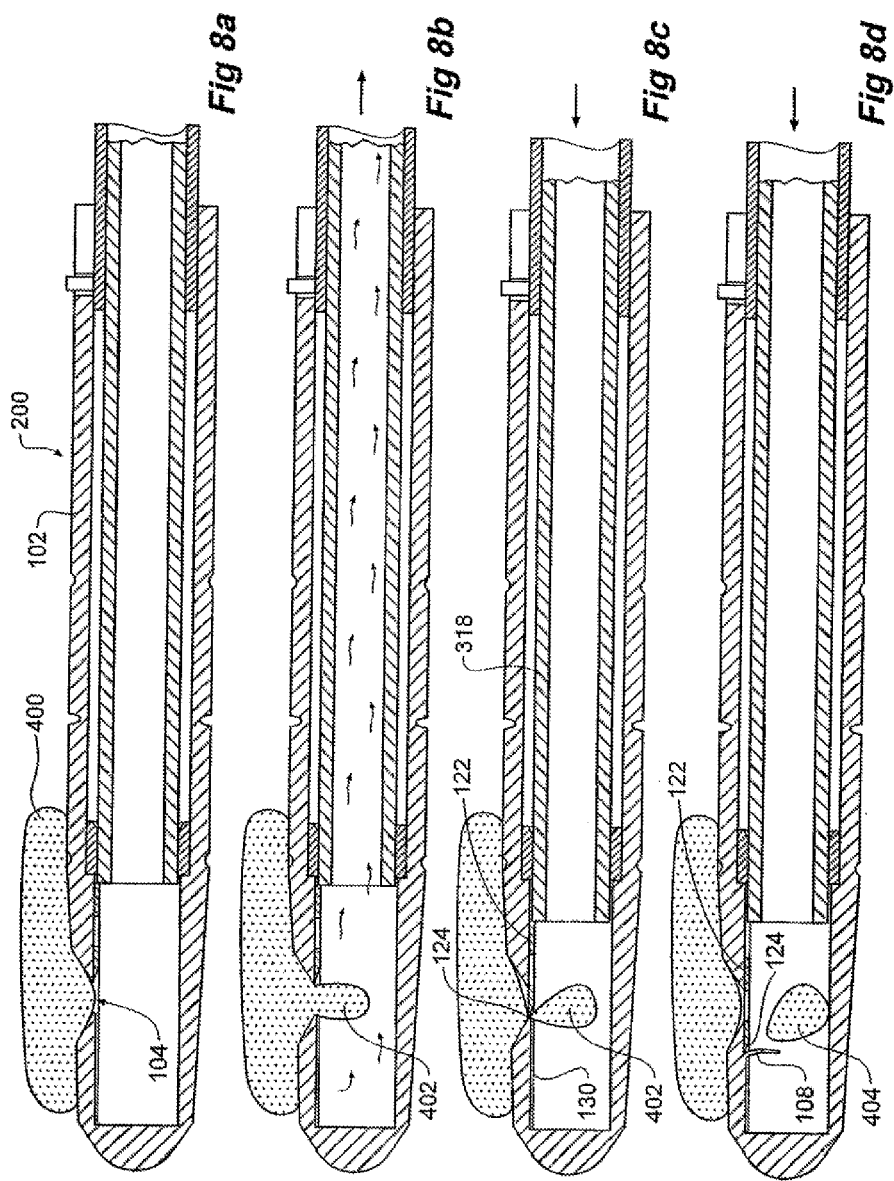

SINGLE USE BIOPSY DEVICE AND METHOD

FIELD OF INVENTION

The present invention relates generally to a single use biopsy device and method for the biopsy of a tissue specimen.

BACKGROUND OF THE INVENTION

Various devices have been used to obtain biopsy samples.

One type of simple biopsy device includes a blade that is located on an end of a rod and a receptacle having an opening for receiving tissue to be biopsied. In use, the rod is used to push the blade into the receptacle so as to sever biopsy tissue that is protruding into the receptacle through the opening. In devices of this type, the blade is removable from the receptacle after use so that the blade, the rod and the receptacle may be cleaned and sterilised for reuse. Unfortunately, once the blade is removed from the receptacle there is a risk that a user of the device may make accidental contact with the blade and thus sustain a "stick injury".

Another biopsy device, for use with an aspiration type biopsy procedure, includes a cylindrical capsule containing a cylindrical spring-activated knife. In devices of this type, tissue is first drawn into an opening in the capsule by way of suction and thereafter the knife is triggered so as to cut the tissue and obtain a biopsy sample. Spring-activated devices of this type are typically used to perform multiple biopsy procedures.

Reusing a biopsy device introduces a number of difficulties. Firstly, if the device is not properly sterilised following each biopsy procedure there is a prospect that further use of the device may lead to infection or cross-contamination.

In addition, cleaning and sterilisation of existing biopsy devices typically requires these devices to be disassembled, and then subsequently reassembled for use. During disassembly, or assembly, the biopsy device may sustain accidental damage that may not be readily detectable to a user, but that may nevertheless render the device unfit, or unsafe, for use, unbeknown to a user. For example, a cutting edge of the blade (or knife) may be damaged in a way that blunts or chips the blade (or knife). In an aspiration biopsy device, such damage may render the device incapable of forming a seal with a biopsy site.

The present invention seeks to provide a single use biopsy device that renders itself non-reusable after performing a biopsy procedure.

SUMMARY OF THE INVENTION

Brief Description of the Drawings

The present invention provides a single use biopsy device, the device including: a receptacle having a port for allowing tissue from a biopsy site to protrude into the receptacle;

a cutter supported in the receptacle and arranged so that when tissue from a biopsy site protrudes into the receptacle through the port the cutter is movable to sever the tissue so as to obtain a biopsy sample; and a stop for arresting the cutter after the cutter has severed the tissue; wherein the arresting of the cutter prevents reuse of the device.

Figure 1:
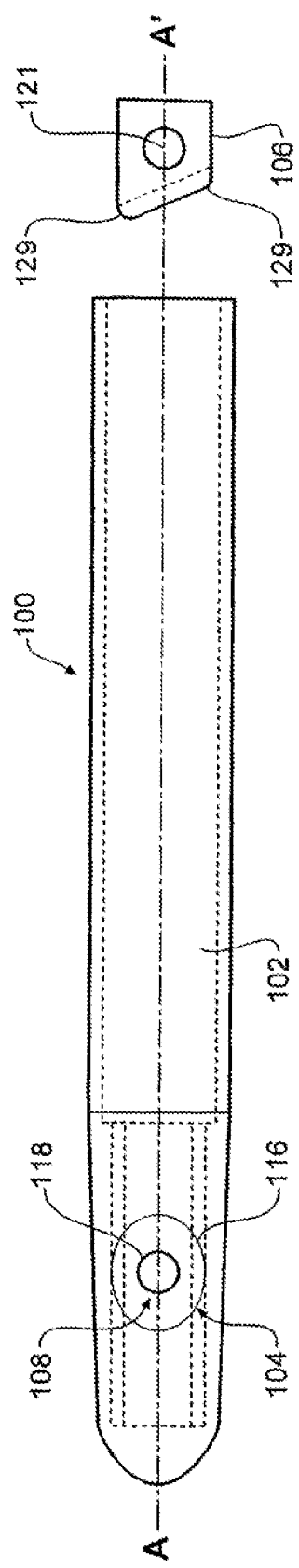

The receptacle may have any suitable shape, the actual shape being dependent upon the type of biopsy procedure for which the device is intended to be used. In an embodiment that is intended to be used for collection of a tissue sample from inside an orifice of a body so as to obtain tissue from a biopsy site therewithin, the receptacle may have an elongated, generally cylindrical exterior shape. In this embodiment, the device preferably includes a cross section having a geometry that is suitable for inserting the device into the orifice of the body. Additionally, the receptacle may include a rounded tip that, in use, tends to part the orifice of the body so as to assist insertion thereinto and thereby reduce the likelihood of unintentional internal damage.

In an alternative embodiment that is intended to be used to obtain tissue from a biopsy site located on the outside of the body, the receptacle shape may have an exterior shape that is suitable for contacting the port against the biopsy site. A biopsy device according to this embodiment may be suitable for obtaining a biopsy of skin tissue, including neoplasms and raised congenital spots (for example, a mole).

The receptacle preferably includes an interior region for containing a biopsy sample obtained by the device. In an embodiment, the interior region is located proximal to the port of the device so that the port opens into the interior region.

The interior region may have any suitable configuration. One suitable configuration may be an enclosed chamber. Another suitable configuration may include an opening for allowing the biopsy sample to be removed from the interior region after use.

In an embodiment that includes an opening for allowing a biopsy sample to be removed from the interior region after use, it is preferred that the device further include an obstruction for obstructing movement of the biopsy sample from the interior region until a user desires to remove the same. That is, it is preferred that the device further include an obstruction that tends to contain the biopsy sample in the interior region.

In one embodiment, the cutter is supported in the receptacle and arranged so that the cutter tends to obstruct the opening so as to reduce the likelihood of the biopsy sample moving from the interior region via the opening. In this form, it is the cutter that then also acts as an obstruction.

The receptacle may be controllably fracturable to provide access to the interior region so as to allow a biopsy sample to be removed therefrom. Indeed, in one embodiment, the receptacle includes at least one recess or zone of weakness allowing the receptacle to fracture in response to a fracturing force to provide improved access for removing the biopsy sample from the interior region. In an embodiment that includes a cylindrically shaped receptacle, each of the recesses or zone of weakness may include one or more circumferentially extending ridges or grooves. However, since the receptacle need not be cylindrical in shape, the recesses or zone of weakness may include one or more ridges or grooves that extend about the longitudinal axis of the receptacle and that have a geometry that corresponds with the cross sectional shape of the receptacle.

In some embodiments, in addition to allowing the receptacle to be controllably fracturable, the recesses or zones of weakness may also provide an indicative function. Indeed, in an embodiment that is intended to be inserted into an orifice of a body so as to obtain a biopsy sample from inside the body, each recess or zone of weakness may be located on an external surface of the receptacle and arranged for indicating a desired depth of insertion. In such an embodiment, it is preferred that the recesses or zones of weakness are uniformly spaced apart.

The receptacle may be manufactured from any suitable material and using any suitable method of construction. One suitable material may include a sterilisable polymer based material, in which case a suitable method of construction may include plastic injection moulding. Another suitable material may include stainless steel. Yet another suitable material may be a ceramic material.

The material may have optical characteristics that are matched to the intended use of the device. For example, where the device is intended to be use to obtain biopsy tissue from a biopsy site located on the outside of the body (for example, skin), the receptacle may be manufactured from a transparent material that allows a user to view the interior region of the receptacle and thus the tissue that protrudes into the receptacle.

A transparent receptacle is particularly advantageous for an embodiment of the biopsy device that is intended to be used to obtain a biopsy sample from a biopsy site located on the outside of the body as it allows a user to visually inspect the tissue to be biopsied prior to severing the tissue. In one embodiment, substantially the entire receptacle is manufactured from a single piece of transparent material. However, in other embodiments the receptacle may be assembled using parts made from different materials. Thus, in one embodiment the receptacle may include a combination of transparent and opaque materials, wherein the transparent material is arranged to provide a viewing window for viewing into the receptacle.

In one embodiment, the cutter is supported in the receptacle so as to be not normally removable therefrom. Supporting the cutter in this way offers additional benefits as it normally prevents the user from handling the cutter and thus reduces the likelihood of the user sustaining an injury from such handling.

The cutter may have any suitable configuration. One suitable configuration may include a cutter having a first edge ('the cutting edge') for severing the tissue. In one embodiment, the cutting edge is angled so that the cutting edge includes a leading portion and a trailing portion so that in use the leading portion makes first contact with the tissue to be severed. The cutter may also include a second edge for abutting against a cutter driver that is operable to move the cutter so as to sever tissue that protrudes through the port. Suitable cutter drivers will be explained in more detail later.

In one embodiment, the cutter has a cylindrical shape. According to this embodiment, the cutting edge and the second edge may each extend around at least a section of respective opposite rims of the cutter. In an embodiment that includes a cylindrical shaped cutter having a cutting edge that extends around at least a section of a rim of the cutter device, the cutter is supported in the receptacle so as to be movable to traverse the cutting edge across the port of the device.

Another suitable cutter configuration may include a cutter having a planar shape. Indeed, according to one embodiment the cutter includes a planar blade having a cutting edge and a second edge that are oppositely arranged. A cutter that includes a planar blade may be supported between guides located in, or on, the receptacle so that the planar blade is slidably positioned therebetween and thus movable over a path defined by the guides. In one embodiment the guides are tracks that are located in, or on, an interior surface of the receptacle so that opposite sides of the cutter are received in the tracks. The tracks may be integrally formed in the interior surface of the receptacle, or alternatively may be separately fitted to the interior surface.

Advantageously, a receptacle that includes integrally formed tracks has a reduced mechanical complexity and thus lower manufacturing costs as compared to tracks that are separately fitted to the interior surface.

In an embodiment, the guides are arranged to engage with the opposite sides of the planar blade so as to restrict movement of the planar blade other than movement directed along the path defined by the guides. In one embodiment, the engagement of the guides with the opposite sides of the planar blade includes a frictional engagement. A guide arrangement that tends to restrict movement of the blade other than movement directed along the path defined by the guides is particularly beneficial as it provides for improved directional control and stability of the planar blade during movement. Such improved directional control and stability tends to reduce the likelihood of undesirable movement of the planar blade that may otherwise prevent severing of the tissue.

It is preferred that the stop be arranged so that after the cutter has severed the tissue to obtain a biopsy sample, the cutting edge of the cutter is embedded into the stop so as to thereby arrest the cutter. The arresting of the cutter by way of embedding the cutting edge in the stop may frictionally capture the cutter so as to normally prevent the cutter from being withdrawn from the stop thereafter. A stop arrangement that permits the cutting edge to be embedded in the stop also provides further benefits. In particular, when the cutting edge of the cutter is embedded in the stop, the cutting edge is rendered normally inaccessible to the user. Thus, such an arrangement reduces the likelihood of injury that may otherwise result where the cutting edge is accessible to the user or other person.

Preferably, the severing of the tissue by the cutter involves an interaction between the cutting edge of the cutter and the stop. According to an embodiment, an interaction of this type may provide two stages, including a first stage in which the cutting edge of the cutter and the stop interact to sever the tissue, and a second stage including the stop arresting the cutter after the tissue has been severed. Thus, the present invention also provides a single use biopsy device, including:

an elongate receptacle having a distal end, a proximal end, and a port located proximal to the distal end for allowing tissue from a biopsy site to protrude into an interior region of the receptacle;

a planar cutter supported inside the receptacle so as to be movable along the longitudinal axis of the receptacle by a cutter driver;

a stop, integral with the port, for interacting with a cutting edge of the cutter to sever the tissue and arrest the cutter;

wherein the arresting of the cutter prevents reuse of the device.

The stop may be located in, or adjacent to, the port of the device so that the stop obstructs the path of the cutter substantially immediately after the cutting edge has traversed the port. In an embodiment, the arresting of the cutter occurs substantially immediately after the cutting edge has traversed the port.

Thus, the present invention also provides a single use biopsy device, including:

a receptacle having a port for allowing tissue from a biopsy site to protrude into the receptacle;

a cutter supported in the receptacle and arranged so that when tissue from a biopsy site protrudes into the receptacle through the port the cutter is movable to sever the tissue so as to obtain a biopsy sample; and a stop for arresting the cutter after the cutter has severed the tissue;

wherein the arresting of the cutter prevents reuse of the device and wherein the stop arrests the cutter substantially immediately after the cutting edge has traversed the port.

A device that includes a stop that is located in, or adjacent to, the port so that the stop obstructs the path of the cutter, provides a severing action that is terminated when the cutter bears against, or embeds into, the stop. Such a severing action is particularly advantageous as it reduces the likelihood of incomplete severing of the tissue that may otherwise lead to tearing of the tissue.

The biopsy device may be used for aspiration biopsy or non-aspiration biopsy procedures. In a simple form, where the biopsy device is intended to be used for non-aspiration biopsy procedure, the receptacle may be adapted to receive a cutter driver so that an edge of the cutter driver abuts against the second edge of the cutter. The cutter driver may be included with the device, or alternatively, it may be a separate component that, in use, is insertable into the receptacle. Thus, the present invention also provides a single use non-aspiration biopsy device including:

a receptacle having a port for allowing tissue from a biopsy site to protrude into the receptacle;

a cutter supported in the receptacle and arranged so that when tissue from a biopsy site protrudes into the receptacle through the port the cutter is movable to sever the tissue so as to obtain a biopsy sample, the cutter being adapted to engage with a cutter driver so that the cutter driver is operable to move the cutter; and a stop for arresting the cutter after the cutter has severed the tissue; wherein the arresting of the cutter prevents reuse of the device and wherein the stop arrests the cutter substantially immediately after the cutting edge has traversed the port.

Alternatively, in an embodiment that is intended for use in an aspiration biopsy procedure, the receptacle may be adapted to receive a suction line that connects the interior region of the receptacle to a suction source that is operable to reduce pressure in the interior region so as to thereby draw the tissue into the interior region.

In one embodiment, the suction source may be included within the device itself. However, in an alternative embodiment the suction source is connectable, or attachable, to the device by way of a suitable suction line.

According to this embodiment, the device preferably includes a seal that is located in the receptacle for slidably receiving a section of the suction line so that in use a hermetic seal is formable between the port and the suction source when the port is substantially entirely in contact with the biopsy site. In use, such an arrangement may provide improved suction control during an aspiration biopsy procedure. Such improved control may allow the device to obtain a biopsy sample having a more predictable, or at least substantially consistent, size for a given procedure and suction source operation.

The seal may be arranged to receive a section of the suction line so that an outside perimeter of the suction line forms a sealed engagement with an inside perimeter of the seal. The seal may be integrally formed with the receptacle or it may be separately fitted to the receptacle.

In an embodiment, the seal is located between the opening and the internal region of the receptacle and has an inside perimeter for sealably engaging with a cutter driver. In such an embodiment, at least a portion of the cutter is located radially inwardly relative to the inside perimeter of the seal for access by a cutter driver having an outside perimeter of substantially the same size as the inside perimeter of the seal. Thus, the present invention also provides a single use aspiration biopsy device, including:

an elongate receptacle having a distal end, a proximal end and an opening located at the proximal end of the receptacle, the receptacle including a port located proximal to the distal end for allowing tissue from a biopsy site to protrude into an interior region of the receptacle;

a cutter supported in the receptacle, the cutter being movable by a cutter driver to sever tissue protruding into the interior region to obtain a biopsy sample for containment in the interior region;

a stop for arresting movement of the cutter to prevent reuse of the device; and a seal located between the opening and the internal region, the seal having an inside perimeter for sealably engaging with a cutter driver; wherein at least a portion of the cutter is located radially inwardly relative to the inside perimeter of the seal for access by a cutter driver having an outside perimeter of substantially the same size as the inside perimeter of the seal.

In an embodiment, the seal is a resilient cylinder that located within the receptacle.

In one embodiment, the suction line may include the cutter driver so that the cutter driver engages with the cutter to thereby render the cutter responsive to movement of the cutter driver in the direction of the stop. According to this embodiment, the cutter driver may include a hollow rod (such as a hollow piston rod).

The present invention also provides an aspiration biopsy system, the system including:

a single use biopsy device, the device including a receptacle having a port for allowing tissue from a biopsy site to protrude into the receptacle, an interior region for containing a biopsy sample obtained by the device, a cutter supported in the receptacle and arranged so that when tissue from a biopsy site protrudes into the receptacle through the port the cutter is movable to sever the tissue so as to obtain a biopsy sample, and a stop for arresting the cutter after the cutter has severed the tissue so that the arresting of the cutter prevents reuse of the device;

a suction line for connecting the interior region of the receptacle to a suction source, the suction source being operable to reduce pressure in the receptacle so as to thereby draw tissue into receptacle so that the tissue protrudes thereinto, the suction line including a cutter driver that is operable to move the cutter;

a seal positioned in the receptacle and arranged to receive a section of the cutter driver so that an outside perimeter of the cutter driver forms a sealed engagement with the seal; wherein the cutter driver is arranged so that an edge of the cutter abuts against an edge of the cutter driver so that the cutter is responsive to movement of the cutter driver in the direction of the stop.

The present invention also provides a method of obtaining a biopsy sample from a biopsy site, including:

obtaining a single use biopsy device, the device including a receptacle having a port for allowing tissue from a biopsy site to protrude into the receptacle, an interior region for containing a biopsy sample obtained by the device, a cutter supported in the receptacle and arranged so that when tissue from a biopsy site protrudes into the receptacle through the port the cutter is movable to sever the tissue so as to obtain a biopsy sample and a stop for arresting the cutter after the cutter has severed the tissue so that the arresting of the cutter prevents reuse of the device; placing the port of the biopsy device against the biopsy site; operating a suction source in fluid communication with the interior region of the receptacle so as to draw tissue from the biopsy site thereinto;

operating a cutter driver to move a cutting edge of the cutter towards the stop to sever the tissue protruding into the interior region through the port to thereby obtain a biopsy sample; and ceasing operation of the cutter driver after the cutter has been arrested by the stop by way of the cutting edge embedding into the stop.

BRIEF DESCRIPTION OF THE DRAWINGS

The present invention will now be described in relation to various embodiments illustrated in the accompanying drawings. However, it must be appreciated that the following description is not to limit the generality of the above description.

Figure 2:
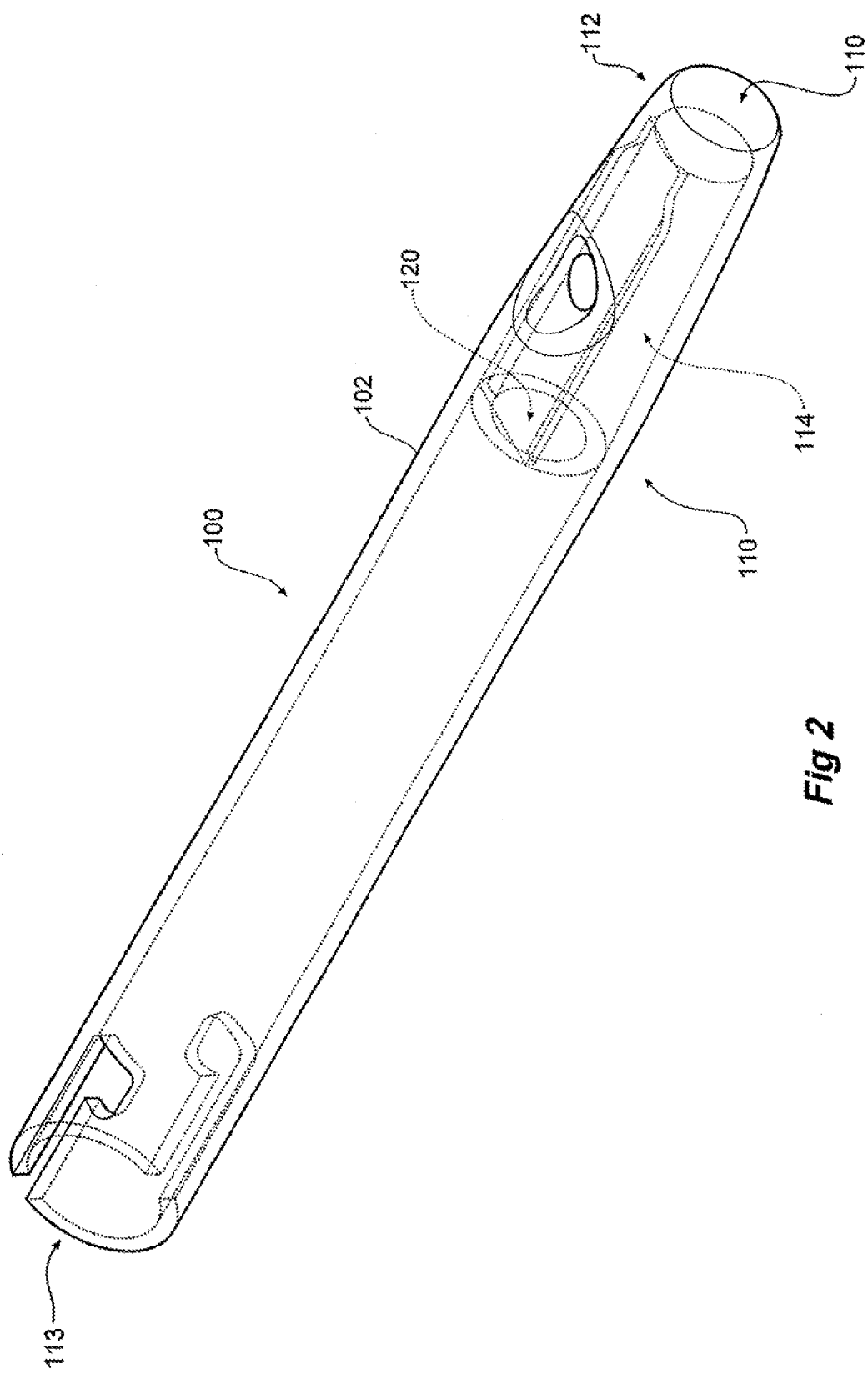
Figure 3A:
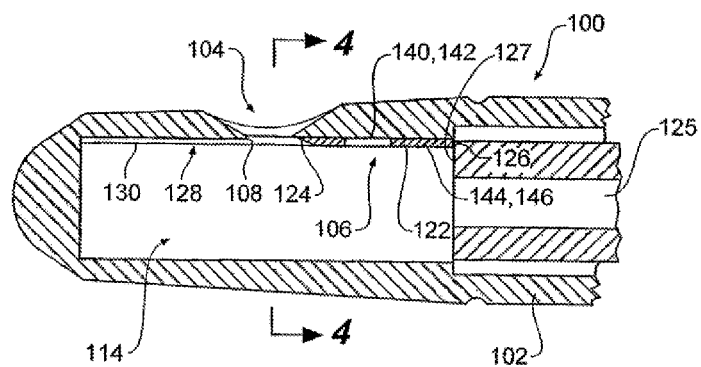
Figure 3B:
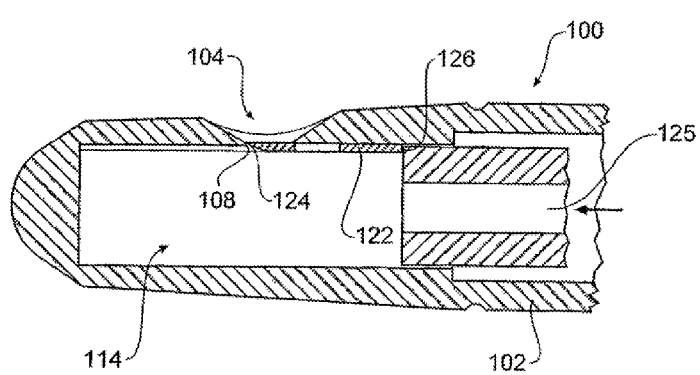
Figure 3C:
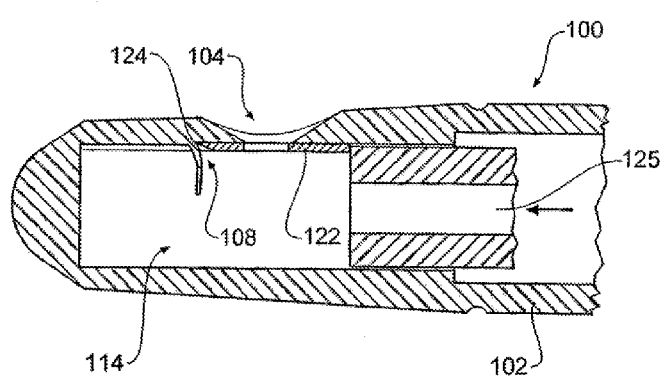
Figure 4A:
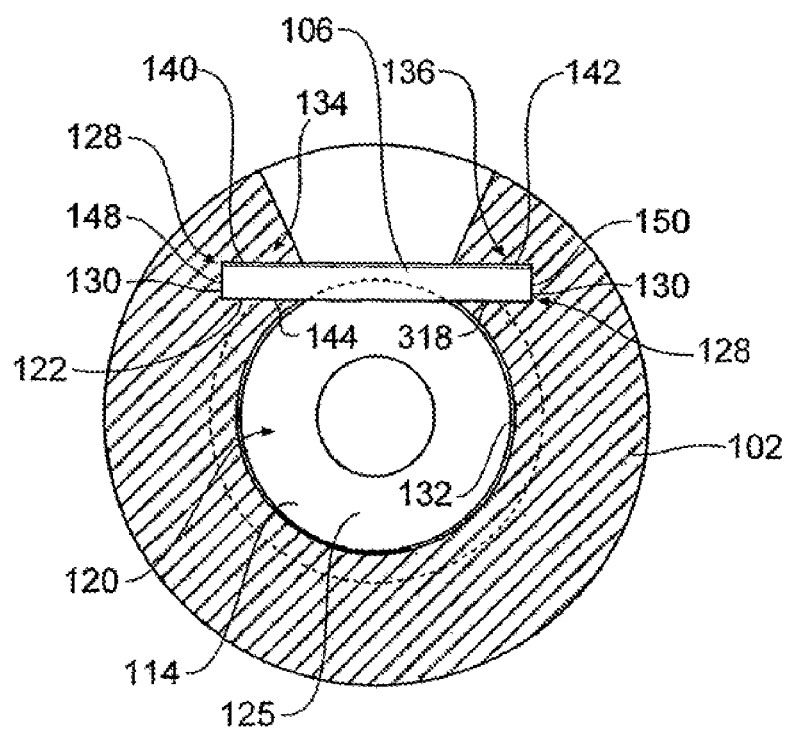
Figure 4B:
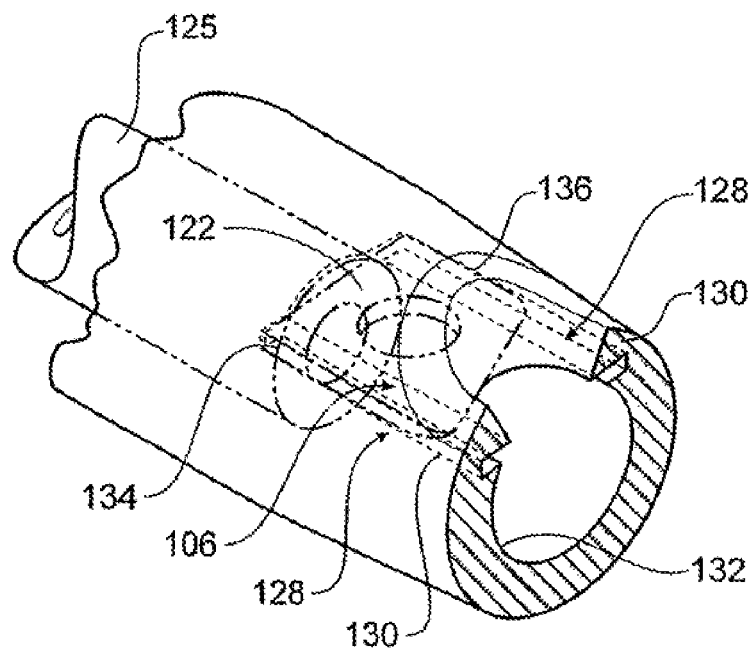
Figure 5:
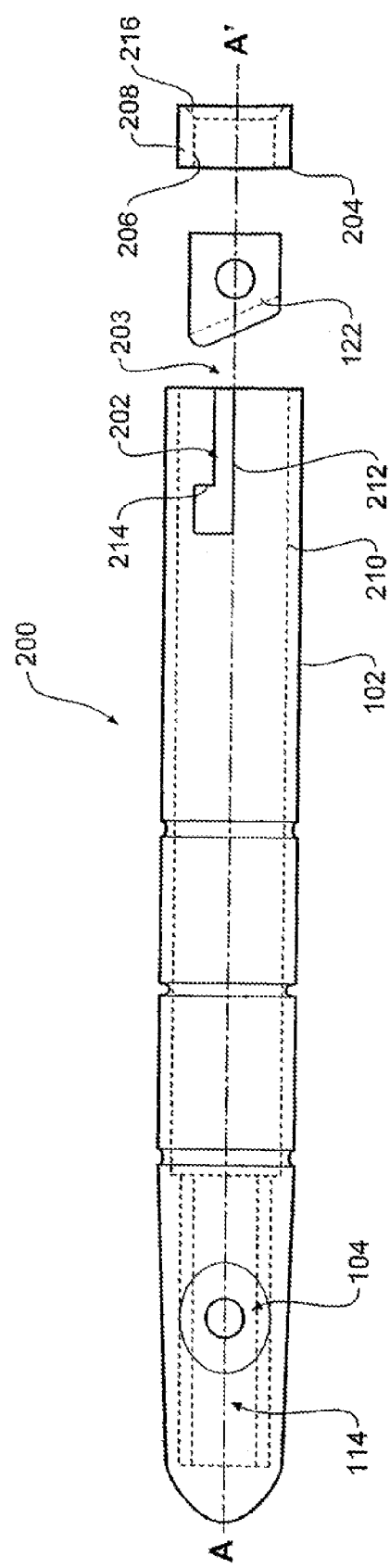
Figure 6:
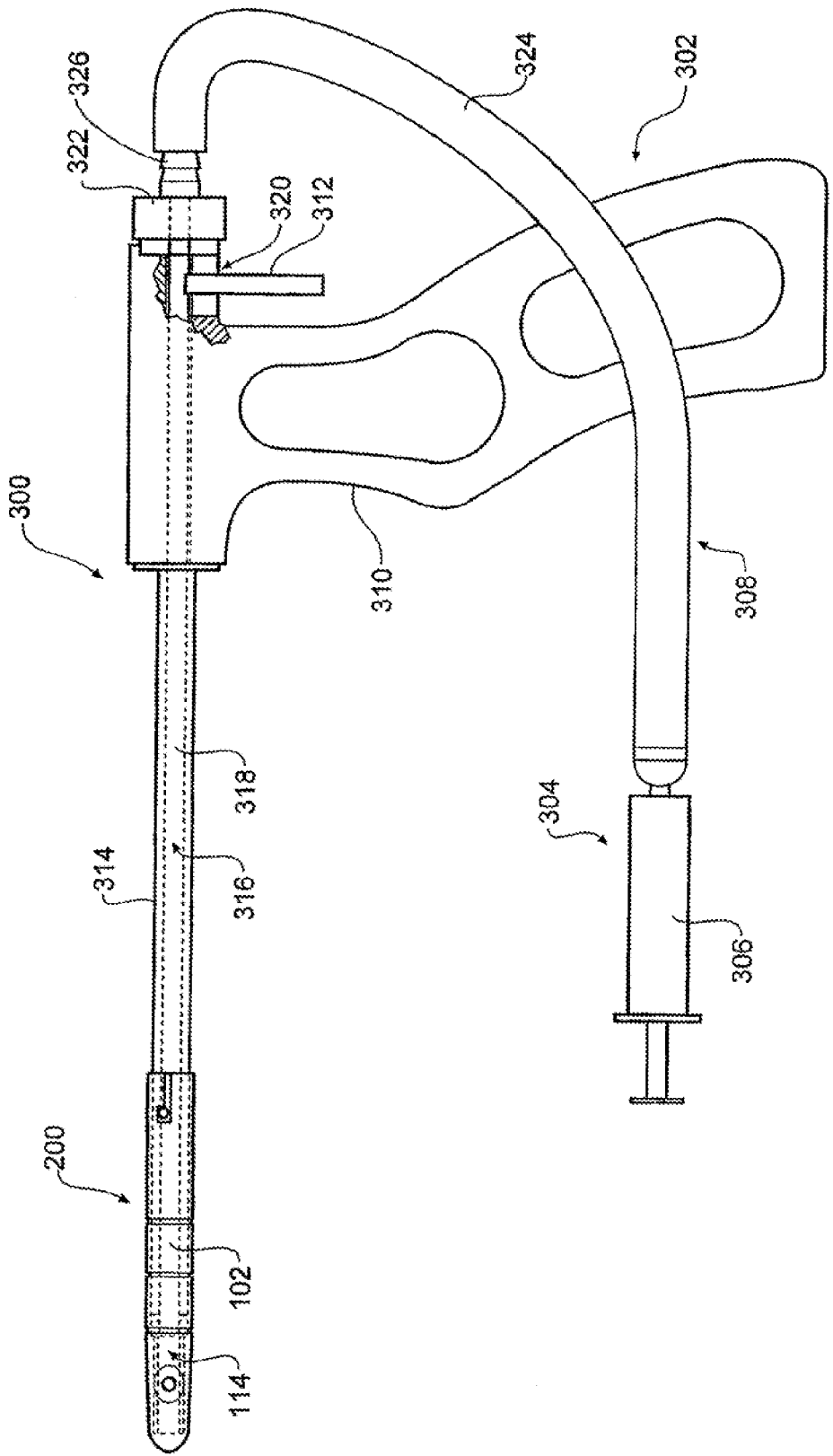
Figure 7A:
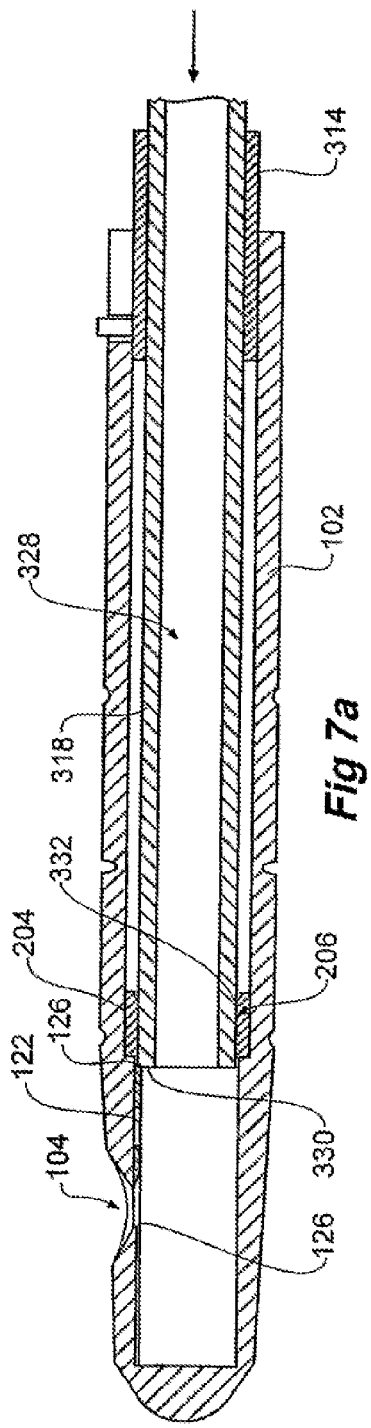
Figure 7B:
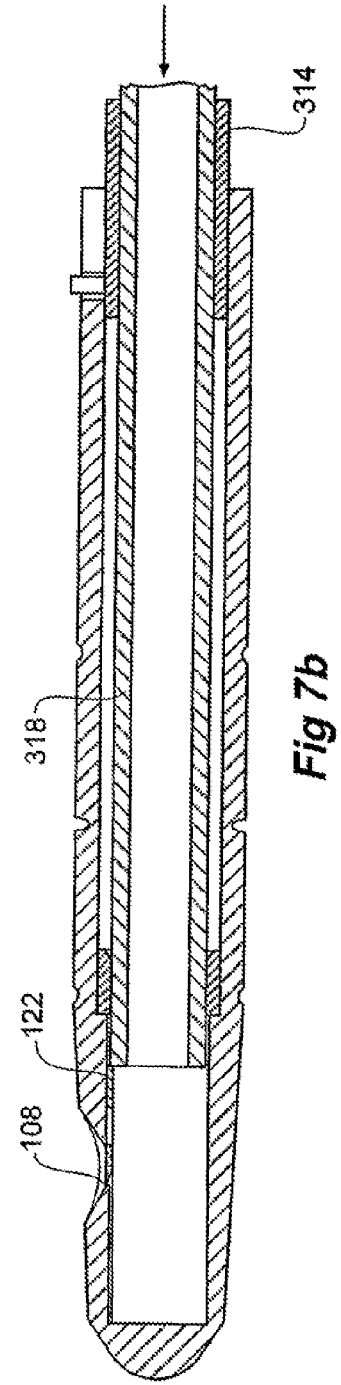
Figure 7C:
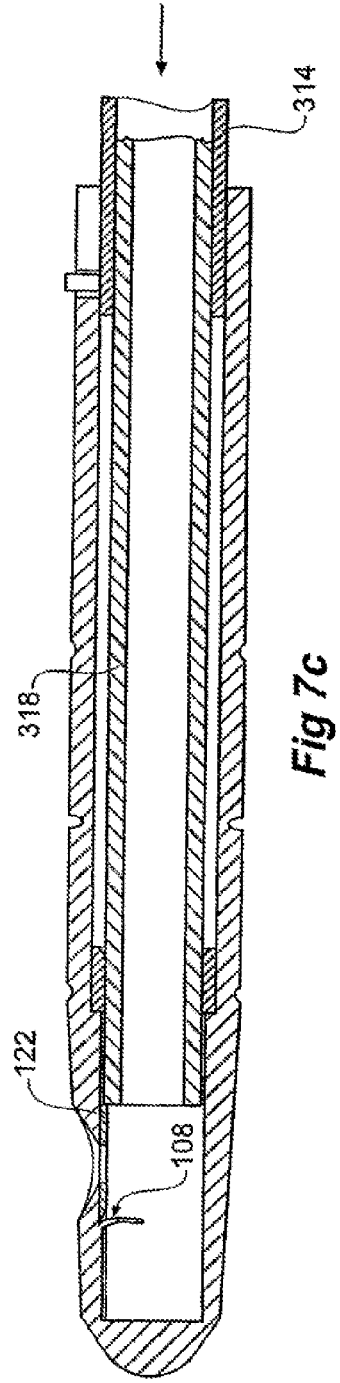
Figure 9A:
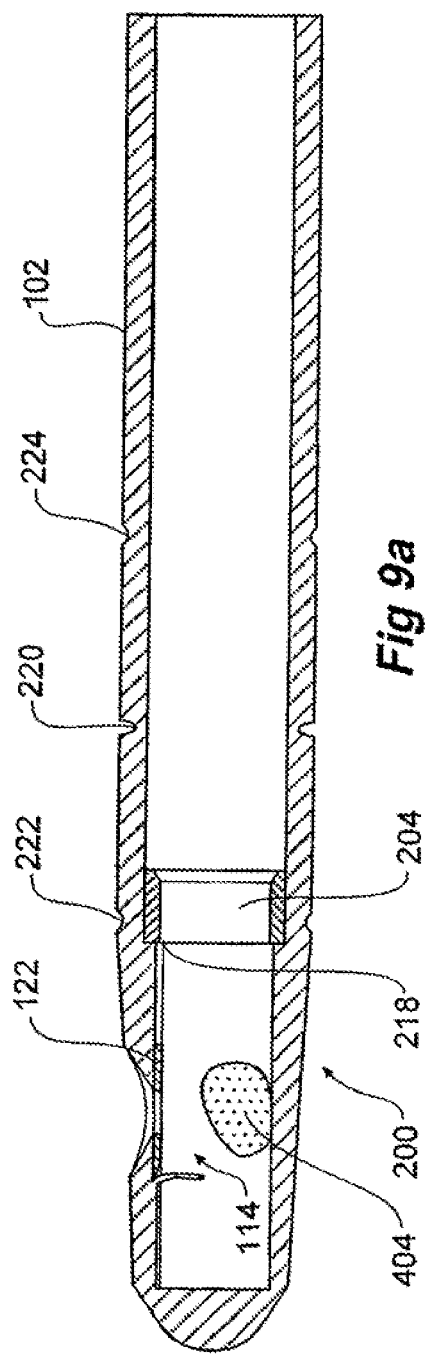
Figure 9B:
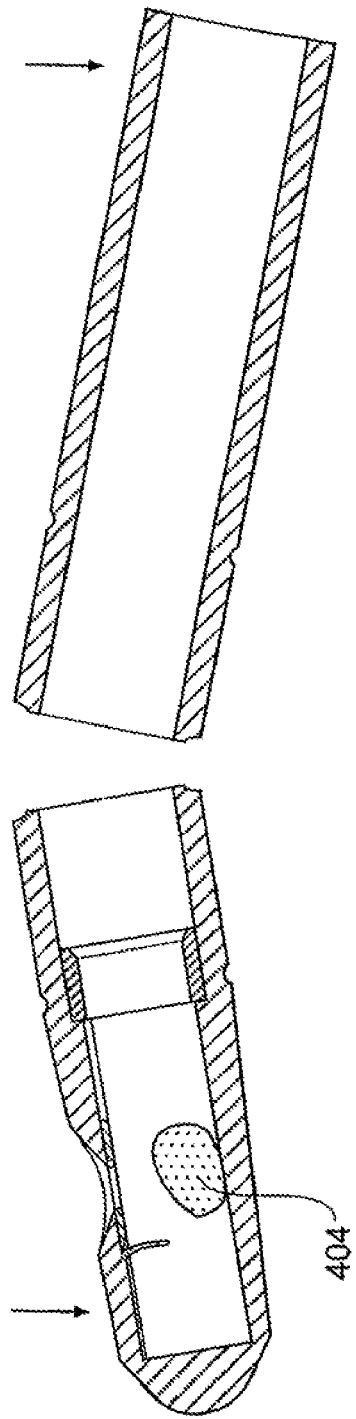

In the drawings:

FIG. 1 shows an exploded top view of a biopsy device according to an embodiment of the present invention;

FIG. 2 shows a perspective view of the receptacle of the biopsy device of FIG. 1;

FIGS. 3A to 3C show partial side cross-sectional views of the biopsy device of FIG. 1 shown with a cutter driver inserted into the receptacle;

FIG. 4A shows a sectional end view of the biopsy device of FIG. 1 shown looking in the direction indicated in FIG. 3A;

FIG. 4B shows a close-up perspective sectional view of the receptacle of the biopsy device of FIG. 1 shown looking in the direction indicated in FIG. 3A;

FIG. 5 shows an exploded top view of a biopsy device according to a second embodiment of the present invention;

FIG. 6 shows an aspiration biopsy system incorporating the biopsy device of FIG. 5;

FIGS. 7A to 7C shows side cross-sectional views of the biopsy device of FIG. 5 during movement of the cutter by a cutter driver of the biopsy system shown in FIG. 6;

FIGS. 8A to 8D show a sequence illustrating the obtaining of a biopsy sample using the biopsy system of FIG. 6;

FIG. 9A shows a side cross sectional view of the biopsy device of FIG. 5 incorporating a recess for fracturing the receptacle to improve access to the internal region; and FIG. 9B shows a side cross sectional view of the biopsy device of FIG. 9A after being fractured to access the internal region.

Figure 10A:
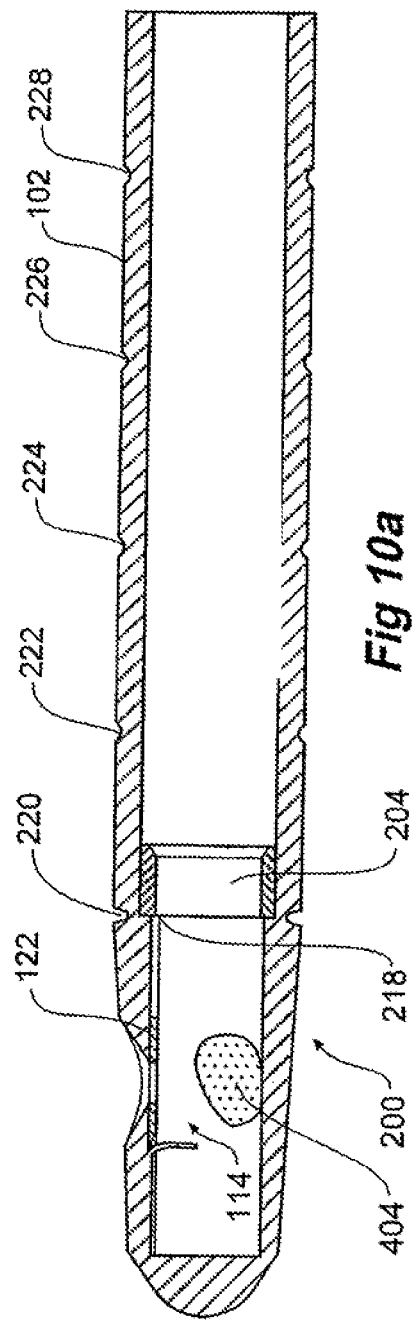
Figure 10B:
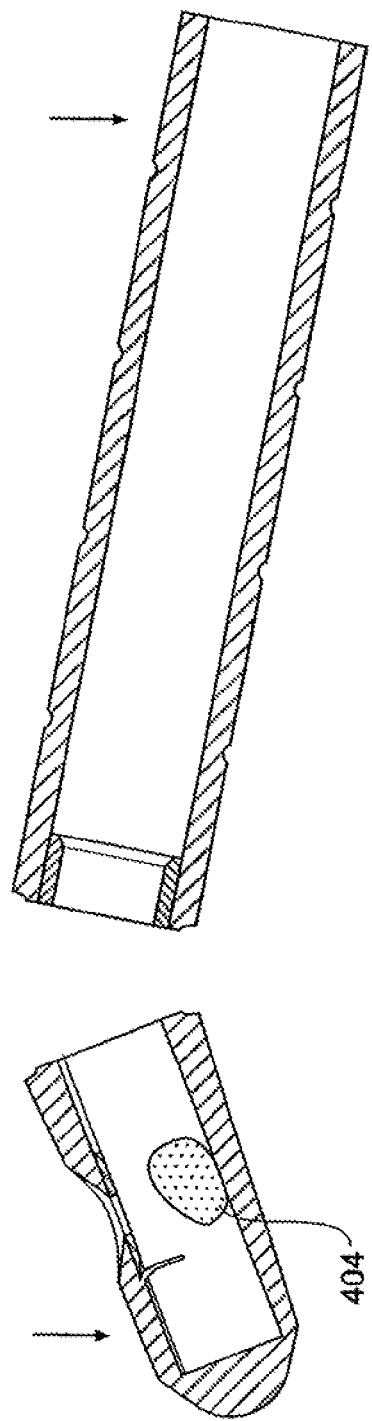

FIG. 10A shows a side cross sectional view of a biopsy device according to another embodiment of the present invention; and FIG. 10B shows a side cross sectional view of the biopsy device of FIG. 10A after being fractured to access the internal region.

DETAILED DESCRIPTION OF THE PREFERRED EMBODIMENT

First Embodiment

FIG. 1 to FIG. 4 show a biopsy device 100 according to a first embodiment of the present invention that is suitable for performing a non-aspiration biopsy procedure. The biopsy device 100 includes a receptacle 102 having a port 104, a cutter 106 and a stop 108.

The illustrated device 100 may be used to perform a biopsy procedure that involves inserting the receptacle 102 into an orifice of body so as to obtain tissue from a biopsy site located inside the body. However, the device 100 is also suitable for performing a biopsy procedure that involves placing the port 104 of the receptacle 102 against the skin of a patient so as to obtain tissue from a biopsy site located externally to the body.

In the present case, the device 100 may be used to performing a rectal biopsy procedure during which a small piece of bowel, or rectal (anal), tissue is obtained for diagnostic examination. Although the illustrated device 100 is intended to be used to perform a rectal biopsy procedure, it will be appreciated that other embodiments of the present invention may be used to perform other types of biopsy procedures on different patients. As will be appreciated, in each case the biopsy site will vary according to the biopsy procedure.

In the present case the biopsy site is located in the rectum. Accordingly, the embodiment illustrated includes a receptacle 102 having an elongated, generally cylindrical exterior shape with an exterior circumference that is suitable for inserting the device into the rectum of a human patient. It is not essential that the receptacle 102 have an generally cylindrical exterior shape and it will be appreciated that other embodiments of the invention may have a shape that varies according to the type of biopsy procedure for which the device is intended to be used.

In the embodiment illustrated, and as is shown in FIG. 2, the receptacle 102 includes a rounded tip 110 that is located at a distal end 112 of the receptacle 102. The receptacle 102 is tapered downwardly towards the distal end 112 so that during insertion of the device 100 into the anus of a patient, the receptacle 102 tends to part the anus to assist insertion into the rectum. The receptacle also includes a proximal end 113.

In the embodiment illustrated, the receptacle 102 is manufactured from a sterilisable polymer based material using a plastic injection moulding process. However, it will be appreciated that the receptacle 102 may be manufactured from any suitable material and using any suitable method of construction.

Turning now to FIG. 3A, the receptacle 102 includes an interior region 114 for containing a biopsy sample obtained by the device 100. In the embodiment illustrated, the interior region 114 is located proximal to the port 104 of the device 100 so that the port 104 opens into the interior region 114.

The port 104 shown here is arranged so as to allow tissue from a biopsy site to protrude into the receptacle 102 when the device 100 is in use. In the present case, tissue from the biopsy site is forced into the interior region 114 by pressing the port 104 against the biopsy site so that tissue from the biopsy site protrudes into the internal region 114. However, in an alternative embodiment, the port 104 may have a geometry that permits tissue from the biopsy site to protrude through the port 104 and into the interior region 114 without the application of force. For example, where the biopsy device 100 is used to biopsy a neoplasm of skin tissue, the port 104 may have a geometry that allows the neoplasm to protrude into the receptacle 102. In this respect, and in the context of this specification, reference to the term "neoplasm" is to be understood to be reference to any abnormal growth of new tissue, whether benign (non-cancerous) or malignant.

As is shown in FIG. 3A, the port 104 has a progressively narrowing cross-section that extends between a generally elliptical lip 116 (ref. FIG. 1) and a generally circular lip 118 (ref. FIG. 1) so that, in use, tissue from a biopsy site tends to sit in, or within, the port 104 to thereby reduce the distance between the tissue and the generally circular lip 118 (ref. FIG. 1) and thus the cutter 106.

In the embodiment illustrated, the port 104 and the stop 108 are integrally formed so that the stop 108 extends around a sector of an inside circumference of the generally circular lip 118 (ref. FIG. 1). The function of the stop 108 will be described in more detail later.

As is shown in FIG. 2 and FIG. 4A, the interior region 114 of the receptacle 102 includes a separate opening 120 for allowing a biopsy sample to be removed from the interior region 114 after it has been severed from the patient. However, it is not essential that the receptacle 102 include a separate opening 120 as in other embodiments a biopsy sample may be removable through a window 121 (Ref. FIG. 1) in the cutter 106, or by fracturing the receptacle 102 so as to access the internal region 114.

In the embodiment illustrated, the cutter 106 includes a window 121 (Ref. FIG. 1) that is arranged so that when the cutter 106 is arrested by the stop 108 the window is aligned with the port 104. In this configuration, a substance (such as a solution) may be flushed into the interior region 114 via the window 121 to thereby assist with removal of a biopsy sample from opening 120.

The cutter 106 is supported in the receptacle 102 and arranged so that the cutter 106 tends to obstruct the opening 120. In this arrangement, the obstruction of the opening 120 by the cutter 106 tends to obstruct movement of the biopsy sample from the interior region 114 (ref. FIG. 3A) until a user desires to remove the same. That is, the cutter 106 tends to assist containment of the biopsy sample within the interior region 114 (ref. FIG. 3A).

As is shown in FIG. 3A, the cutter 106 is a planar blade 122 that includes a first edge 124 ('the cutting edge') for severing the tissue and a second edge 126 for abutting against a cutter driver that is operable to move the cutter 106 so as to sever tissue that protrudes through the port 104.

As is shown in FIG. 3A, in the present case, a suitable cutter driver includes a hollow rod 125 that is insertable into the receptacle 102 through an opening (not shown) so that a bearing edge 127 of the hollow rod 125 contacts the second edge 126 of the planar blade 122 and is operable by a user to move the planar 20 blade 122 towards the stop 108.

Referring to FIG. 4B, the planar blade 122 is shown as being supported between guides 128 (shown here as tracks 130) that are located in the receptacle 102 so that the planar blade 122 is slidably positioned therebetween and thus movable over a path defined by the guides 128. As is shown in FIG. 1, the planar blade 122 includes corners 129 that are shaped so as to reduce the likelihood of the corners 129 "digging into" the guides 128 during use and thus prematurely arresting the planar blade 122 before severing of a tissue sample. In the present case, the corners 129 have a rounded shape.

As is shown in FIG. 4B, the tracks 130 are formed in an interior surface 132 of the receptacle 102 so that opposite sides 134, 136 of the planar blade 122 are received in the respective track 130. Moreover, and as is shown in FIG. 3B, in the embodiment illustrated the tracks 130 are arranged substantially parallel with the longitudinal axis (ref. FIG. 1, line A-A') of the receptacle 102 and positioned so that the cutting edge 124 of the planar blade 122 collides with the stop 108 substantially immediately after the cutting edge 124 of the planar blade 122 has traversed the port 104.

Referring again to FIG. 4B, in the embodiment illustrated, the tracks 130 are arranged to engage with respective opposite sides 134, 136 of the planar blade 122 so as to restrict movement of the planar blade 122 other than movement directed along the path defined by the tracks 130. Indeed, in the present case, the engagement of the tracks 130 with the opposite sides 134, 136 of the planar blade 122 is provided by way of a frictional engagement that tends to resist movement of the planar blade 122 in a direction transverse to the path, but allows movement of the planar blade 122 along the path.

The frictional engagement is provided by way of the tracks 130 engaging with the opposite sides 134, 136 of the planar blade 122 so that there is substantially no clearance between tracks 130 and the opposite sides 134, 136 over substantially the entire length of the planar blade 122. Indeed, and as is shown in FIG. 4A, in the embodiment illustrated, the engagement of the tracks 130 with the opposite sides 134, 136 of the planar blade 122 provides an engagement wherein top surfaces 140, 142 bottom surfaces 144, 146 and side surfaces 148, 150 of respective opposite sides 134, 136 of the planar blade 122 each contact a respective portion of a respective track 130.

As is shown in FIG. 3A, the top surfaces 140, 142, bottom surfaces 144, 146 and side surfaces 148, 150 (ref. FIG. 4A) of respective opposite sides 134, 136 (ref. FIG. 4A) of the planar blade 122 each contact a respective portion of a respective track 130 over substantially the entire length of the planar blade 122.

Frictional engagement of the tracks 130 with the opposite sides 134, 136 of the planar blade 122 provides for improved directional control and stability of the planar blade 122 during movement. Such improved directional control and stability tends to reduce the likelihood of undesirable movement of the planar blade 122 that may otherwise prevent severing of the tissue.

Returning again to FIG. 3A, the stop 108 is located adjacent to the port 104 of 5 the device 100 and arranged so that the stop 108 obstructs the path of the planar blade 122 substantially immediately after the cutting edge 124 has traversed the port 104. In the present case, the stop 108 is arranged so as to extend from the generally circular lip 118 (ref. FIG. 1) of the port 104 so that the stop 108 is located in the path of the planar blade 122. Thus, and as is shown in FIG. 3C, in the embodiment illustrated, the arresting of the planar blade 122 occurs substantially immediately after the cutting edge 124 has traversed the port 104.

A device 100 that includes a stop 108 that is located so as to obstruct the path of the planar blade 122 provides a severing action that is terminated when the cutting edge 124 of the planar blade 122 bears against, or embeds into, the stop 108. Thus, the severing of the tissue by the cutter 106 involves an interaction between the cutting edge 124 of the cutter 106 and the stop 108. In particular, in the illustrated embodiment, the interaction between the cutting edge 124 of the cutter 106 and the stop 108 involves two stages, namely, a first stage in which the cutting edge 124 of the cutter 106 and the stop 108 interact to sever the tissue, and a second stage in which the stop 108 arrests the cutter 106 after the tissue has been severed. The interaction between the cutting edge 124 and the stop 106 to sever the tissue is particularly advantageous as it reduces the likelihood of incomplete severing of the tissue that may otherwise lead to tearing of the tissue, or jamming of tissue in the region located between the circular lip 118 (ref. FIG. 1) and the planar blade 122 (ref. FIG. 1).

Turning now to FIG. 38 and FIG. 3C, in the embodiment illustrated, the stop 108 is arranged so that after the planar blade 122 has severed the tissue to obtain a biopsy sample, the cutting edge 124 of the planar blade 122 embeds into the stop 108 so as to thereby arrest the planar blade 122.

Advantageously, the arresting of the planar blade 122 by way of embedding the cutting edge 124 into the stop 108 captures the planar" blade 122 so as to normally prevent the planar blade 122 from being withdrawn from the stop 108 thereafter. In addition, because the stop 108 shown here is integral with the port 104, the arresting of the planar blade 122, by way of the cutting edge 124 embedding into the stop 108, damages the port 104. Thus, in the illustrated embodiment the arresting of the cutter 106 prevents, in two ways, the device from being reused. Firstly, the embedding of the cutter 106 into the stop 108 tends to capture the cutter 106 so as to normally prevent the cutter 106 from being withdrawn from the stop 108 thereafter. Secondly, the embedding of the cutter 106 cuts the stop 108, and thus the port 104, and so damages the port 104. In some embodiments, damage to the port 104 may be sufficient to render the device 100 non-reusable. In one embodiment, the damage to the port 104 is visible to a user by inspection of the port.

A stop 108 arrangement that permits the cutting edge 124 to be embedded in the stop 108 also provides further benefits. In particular, when the cutting edge 124 of the planar blade 122 is embedded in the stop 108, the cutting edge 124 is rendered normally inaccessible to a user. Thus, such an arrangement reduces the likelihood of injury that may otherwise result where the cutting edge 124 is accessible to the user or other person.

Second Embodiment

FIG. 5 to FIG. 9 show a second embodiment of a biopsy device 200 according to the present invention. The second embodiment is suitable for performing an aspiration biopsy procedure and thus is configured so that tissue from a biopsy site is able to be drawn into the interior region 114 by reducing pressure in the internal region 114 of the device 200.

As is shown in FIG. 5, a device 200 according to the second embodiment of the present invention includes features described in relation to the first embodiment, namely a receptacle 102, a port 104 and a planar blade 122. However, the device 200 of the second embodiment further includes a connector 202 and a seal 204. As is shown, the connector 202 extends axially inwardly from an opening 203.

The seal 204 shown here is inserted into the receptacle 102 and arranged to allow the device 200 to be connected to a tool (not shown) for inserting and operating the device 200 so that a hermetic seal is formed between the port 104 and a suction source (not shown) when the port 104 is sealed by tissue from a biopsy site. Thus, the seal 204 locates between the opening 203 and the internal region 114. The tool and the suction source will be described in more detail with reference to FIG. 6 later.

In the present case, and still referring to FIG. 5, the seal 204 is shown as a cylindrical seal having an inside circumferential surface 206 and an outside circumferential surface 208. The seal 204 is received within the receptacle 102 so that the outside circumferential surface 208 contacts an inside circumferential wall 210 of the receptacle 102 to thereby make a sealed contact therewith.

As is shown in FIG. 7a, at least a portion of the planar blade 122 is located radially inwardly relative to the inside perimeter of the seal 204 (shown here as the inside circumferential surface 206) of the seal 204 for access by a cutter driver having an outside perimeter of substantially the same size as the inside perimeter of the seal 204.

The inside circumferential surface 206 of the seal 204 is arranged to slidably receive a suction line (not shown) so that the suction line sealably engages with the inside circumferential surface 206 of the seal 204.

The connector 202 is shown as a slot 212 for receiving a pin (not shown) of the tool. The slot 212 shown here includes a shoulder 214 that is arranged so that when the device 200 is attached to the tool (not shown), a tool pin rests against the shoulder 214 so as to normally prevent the device 200 from detaching from the tool.

FIG. 6 illustrates a biopsy system 300 that incorporates a biopsy device 200 according to the second embodiment of the invention. As is shown, the system 300 includes the device 200, a tool 302, a suction source 304 (shown here as a syringe 306) and a suction line 308 that connects the interior region 114 of the device 200 to the syringe 306.

The tool 302 shown here includes a handle 310 that assist with the insertion of the device 200 into a body orifice and a trigger 312 for controlling movement of the planar blade 122 (ref. FIG. 7A). The illustrated tool 302 also includes a rigid tube 314 and a cutter driver 316 (shown here as a hollow rod 318). The hollow rod 318 shown here is fixedly connected to the trigger 312 and slidably located within the rigid tube 314.

The handle 310 includes a slot 320 for receiving an end of the trigger 312. A lock nut 322 is fitted to the handle 310 so as to close an open end of the slot 320 and thus define a region of movement for the trigger 312 that is bounded by the slot 320 and the lock nut 322. The trigger 312 and the hollow rod 318 are fixedly connected so that movement of the trigger 312 in the slot 320 causes a corresponding movement of the hollow rod 318.

The suction line 308 shown here includes a flexible tube 324 and the hollow rod 318 in an arrangement that allows the syringe 306 to be operable to reduce pressure in the internal region 114 of the receptacle 102. That is, in the illustrated embodiment, the suction source (shown here as syringe 306) is in fluid communication with the interior region 114 of the receptacle.

In the embodiment illustrated, the hollow rod 318 is connected to the flexible tube 324 using a connector 326 that is integral with the hollow rod 318. As is shown in FIG. 7A a section 328 of the hollow rod 318 extends into the receptacle 102. The section 328 that extends into the receptacle 102 includes a bearing edge 330 that contacts against the second edge 126 of the planar blade 122 so that planar blade 122 is responsive to movement of the hollow rod 318 in the direction of the stop 108. As is shown in FIGS. 7A to 7C, in the illustrated configuration, the hollow rod 318 is operable, under the control of the trigger 312 (ref. FIG. 6), to move the planar blade 122 towards the stop 108.

Referring again to FIG. 7A, the section of the hollow rod 318 that extends into the receptacle 102 is received within the receptacle 102 so as to be sealably received therein. Indeed, in the present case, the seal 204 sealably receives an end of the hollow rod 318 so that in use a hermetic seal is formed between the port 104 and the syringe 306 (ref. FIG. 6) when the port 104 is substantially entirely in contact with the biopsy site, so that the biopsy site seals the port 104. As is shown in FIG. 5, the seal 204 includes a chamfer 216 that provides a "lead in" for guiding the hollow rod 318 into the seal 204.

As is shown in FIG. 7A, the receiving of a section 328 of the hollow rod 318 by the seal 204 includes an outside surface 332 of the hollow rod 318 forming a sealed engagement with the inside circumferential surface 206 of the seal 204 so that the hollow rod 318 is slidable in the seal 204.

Advantageously, in the illustrated device 200, the seal 204 also performs a secondary function. Indeed, and as is shown in FIG. 9A, the seal 204 is located behind the planar blade 122 so as to be located proximal to near ends 218 of the tracks 130 and thereby restrict the planar blade 122 from moving out therefrom. Such a configuration advantageously renders the planar blade 122 normally non-removable from the device 200. Supporting the planar blade 122 in this way offers additional benefits as it normally prevents the user from handling the planar blade 122 and thus reduces the likelihood of the user sustaining an injury from such handling.

In the present case, the supporting of the planar blade 122 in the receptacle 102 so as to render the planar blade 122 normally non-removable therefrom is achieved be achieved using the seal 204. However, it will be appreciated that any suitable arrangement may be used.

Referring now to FIGS. 8A to 8D, operating the biopsy system that incorporates a biopsy device 200 in accordance with the second embodiment preferably includes the following steps:

1. Placing the port 104 of the biopsy device 200 against the tissue of a biopsy site 400;

2. Actuating the syringe 306 (ref. FIG. 6) so as to draw tissue 402 from the biopsy site 400 into the interior region 114 of the receptacle 102 so that the tissue 402 protrudes into the receptacle 102;

3. Using the trigger 312 (ref. FIG. 6) to actuate the hollow rod 318 to move the planar blade 122 along a path defined by the tracks 130 so as to sever the tissue 402;

4. Continue moving the planar blade 122 using the hollow rod 318 until the cutting edge 124 of the planar blade 122 is embedded into the stop 108.

5. Removing the biopsy sample 404 from receptacle 102.

The receptacle 102 may be controllably fracturable to provide access to the interior region 114 so as to allow the biopsy sample 404 to be removed therefrom. Indeed, as is shown in FIG. 9A and FIG. 9B, one form of a receptacle 102 according to the second embodiment includes a recess 220, or line of weakness (shown here as a circumferentially extending groove) that is arranged to allow the receptacle 102 to fracture along the groove to fracture in response to a fracturing force thereby providing improved access to the interior region for removing the biopsy sample 404 therefrom.

Advantageously, in addition to allowing the receptacle 102 to be controllably fracturable, the recess 220 may also provide an indicative function. Indeed, where the device 200 is inserted into an orifice of a body so as to obtain a biopsy sample from inside the body I the recess 220 may be located on an external surface of the receptacle and arranged for indicating the desired depth of insertion into the orifice. As is shown, the receptacle 102 also includes recesses 222, 224 for providing an indication of the depth of insertion into the orifice.

The recess 220 for allowing the receptacle 102 to be controllably fracturable may be located at any suitable position that allows access to the interior region 114 for removal of the biopsy sample 404. Thus, although in FIG. 9a the recess 200 is shown positioned on an opposite side of the seal 204 to the interior region 114, it need not be. Indeed, and as is shown in FIG. 10a and FIG. 10b, the recess 220 may just as easily be located on the same side of the seal 204 as the interior region 114.

It is envisaged that a biopsy device according to an embodiment the invention that includes a recess 220 located on the same side of the seal 204 as the interior region 114 may provide further benefits in that the seal 204 would not obstruct the removal of the biopsy sample 404 from the interior region 114 after fracturing of the device 200.

In relation to the indicative recesses 222, 224 (ref. FIG. 9a), in other embodiments of the present invention, the recesses 222, 224 may have an arrangement that is different to that illustrated in FIG. 9a. Indeed, other embodiments of the present invention may include a different number of, or differently positioned, indicative recesses. For example, and as is shown in FIG. 10a, a biopsy device according to the present invention may include additional spaced apart recesses 226 and 228 arranged along the length of the device 200. A device including additional spaced apart recesses 226, 228 may be useful for conducting a biopsy procedure in which the device 200 is required for a deeper depth of insertion.

Although the present invention has been described in terms of the presently preferred embodiments, it is to be understood that the disclosure is not to be interpreted as limiting. Various alterations and modifications will no doubt become apparent to the skilled in the art after having read the above disclosure.

The invention claimed is:

1. A single use biopsy device including:
    a receptacle having a port for allowing tissue from a biopsy site to protrude into the receptacle;
    a cutter supported in the receptacle and arranged so that when tissue from a biopsy site protrudes into the receptacle through the port the cutter is movable to sever the tissue so as to obtain a biopsy sample; and
    a stop for arresting the cutter after the cutter has severed the tissue;
    wherein the arresting of the cutter by the stop prevents reuse of the device, the cutter including a cutting edge for interacting with the stop to sever the tissue.

2. A biopsy device according to claim 1 wherein the receptacle is controllably fracturable to access the interior region of the receptacle.

3. A biopsy device according to claim 2 wherein the receptacle includes at least one recess or zone of weakness allowing the receptacle to controllably fracture in response to a fracturing force.

4. A biopsy device according to claim 3 wherein the receptacle is elongate and the least one recess or zone of weakness includes one or more ridges or grooves extending about the longitudinal axis of the receptacle.

5. A biopsy device according to claim 3 wherein the receptacle is cylindrical and the recess or zone of weakness include one or more circumferentially extending ridges or grooves.

6. A biopsy device according to claim 3 wherein the recess or zone of weakness are located on an external surface of the receptacle.

7. A biopsy device according to claim 6 wherein the recesses or zones of weakness are uniformly spaced apart to provide indicators for indicating a depth of insertion of the device into an orifice.

8. A biopsy device according to claim 1 wherein the receptacle includes a transparent region for allowing a user to view the interior region of the receptacle.

9. A biopsy device according to claim 1 wherein the cutter is supported in the receptacle so as to be normally not removable therefrom.

10. A single use biopsy device including:
    a receptacle having a port for allowing tissue from a biopsy site to protrude into the receptacle;
    a cutter supported in the receptacle and arranged so that when tissue from a biopsy site protrudes into the receptacle through the port the cutter is movable to sever the tissue so as to obtain a biopsy sample; and
    a stop for arresting the cutter after the cutter has severed the tissue;
    wherein the arresting of the cutter by the stop prevents reuse of the device, and, wherein the cutter includes a planar blade.

11. A biopsy device according to claim 10 wherein the cutter includes a cutting edge for interacting with the stop to sever the tissue.

12. A biopsy device according to claim 11 wherein the cutter includes an edge for abutting with a cutter driver operable to move the cutter towards the stop.

13. A single use biopsy device including:
   a receptacle having a port for allowing tissue from a biopsy site to protrude into the receptacle;
   a cutter supported in the receptacle and arranged so that when tissue from a biopsy site protrudes into the receptacle through the port the cutter is movable to sever the tissue so as to obtain a biopsy sample; and
   a stop for arresting the cutter after the cutter has severed the tissue;
   wherein the arresting of the cutter by the stop prevents reuse of the device, and, wherein the cutter includes a planar blade, the planar blade including a cutting edge for interacting with the stop to sever tissue protruding through the port and an edge for abutting against a cutter driver operable to move the cutter towards the stop.

14. A biopsy device according to claim 13 wherein the planar blade is supported between guides located in the interior region of the receptacle so that the planar blade is slidably positioned therebetween to move over a path defined by the guides.

15. A biopsy device according to claim 14 wherein the guides include tracks located in, or on, an interior surface of the interior region so that opposite sides of the cutter are received in the tracks.

16. A biopsy device according to claim 15 wherein the tracks are integrally formed in the interior surface of the receptacle.

17. A biopsy device according to claim 15 wherein the tracks are fitted to the interior surface.

18. A biopsy device according to claim 14 wherein the guides are arranged to receive opposite sides of the planar blade to restrict movement of the planar blade other than movement directed along the path defined by the guides.

19. A single use biopsy device including:
   a receptacle having a port for allowing tissue from a biopsy site to protrude into the receptacle;
   a cutter supported in the receptacle and arranged so that when tissue from a biopsy site protrudes into the receptacle through the port the cutter is movable to sever the tissue so as to obtain a biopsy sample; and
   a stop for arresting the cutter after the cutter has severed the tissue;
   wherein the arresting of the cutter by the stop prevents reuse of the device, and, wherein the stop is arranged so that, after the cutter has severed the tissue to obtain a biopsy sample, the cutting edge of the cutter embeds into the stop to arrest the cutter.

20. A biopsy device according to claim 1 wherein the cutting edge of the cutter is arranged to interact with the stop to sever tissue protruding into the interior region through the port and wherein the cutting edge of the cutter embeds into the stop to arrest the cutter after the cutter has severed the tissue.

21. A biopsy device according to claim 20 wherein the embedding of the cutting edge into the stop captures the cutter so as to normally prevent the cutter from being withdrawn from the stop thereafter.

22. A biopsy device according to claim 1 wherein the stop is located in, or adjacent to, the port so as to obstruct the path of the cutter substantially immediately after the cutting edge has traversed the port.

23. A single use biopsy device including:
   a receptacle having a port for allowing tissue from a biopsy site to protrude into the receptacle;
   a cutter supported in the receptacle and arranged so that when tissue from a biopsy site protrudes into the receptacle through the port the cutter is movable to sever the tissue so as to obtain a biopsy sample; and
   a stop for arresting the cutter after the cutter has severed the tissue;
   wherein the arresting of the cutter prevents reuse of the device and wherein the stop arrests the cutter substantially immediately after the cutting edge has traversed the port, wherein the cutter and the stop are arranged to sever the tissue when the cutter bears against, or embeds into, the stop.

24. A device according to claim 23 wherein the cutter includes a cutting edge that is movable towards the stop over a path of movement so as to provide a severing action therebetween, the stop obstructing the path of movement and being cuttable by the blade so that the arresting of the cutter includes the cutting edge cutting into the stop to embed thereinto.

25. A device according to claim 23 wherein the receptacle includes a receiving portion for receiving a cutter driver operable to move the cutter to sever the tissue.

26. A single use biopsy device, including:
   an elongate receptacle having a distal end, a proximal end, and a port located proximal to the distal end for allowing tissue from a biopsy site to protrude into an interior region of the receptacle;
   a planar cutter supported inside the receptacle so as to be movable along the longitudinal axis of the receptacle by a cutter driver; and
   a stop, integral with the port, for interacting with a cutting edge of the cutter to sever the tissue and arrest the cutter;
   wherein the arresting of the cutter prevents reuse of the device.

27. A device according to claim 26 wherein the arresting of the cutter damages the port.

28. A device according to claim 26 further including:
   a seal located between the opening and the internal region, the seal having an inside perimeter for sealably engaging with a cutter driver operable to move the cutter towards the stop;
   wherein at least a portion of the cutter is located radially inwardly relative to the inside perimeter of the seal for access by a cutter driver having an outside perimeter of substantially the same size as the inside perimeter of the seal.

29. A single use aspiration biopsy device, including:
   an elongate receptacle having a distal end and a proximal end, the receptacle including a port located proximal to the distal end for allowing tissue from a biopsy site to protrude into an interior region of the receptacle and an opening located at the proximal end for receiving a cutter driver;
   a cutter supported in the receptacle, the cutter being movable by a cutter driver to sever tissue protruding into the interior region to obtain a biopsy sample for containment in the interior region;
   a stop for arresting movement of the cutter to prevent reuse of the device; and
   a seal located between the opening and the internal region, the seal having an inside perimeter for sealably engaging with a cutter driver;

wherein at least a portion of the cutter is located radially inwardly relative to the inside perimeter of the seal for access by a cutter driver having an outside perimeter of substantially the same size as the inside perimeter of the seal, and wherein the cutter and the stop are arranged to sever the tissue when the cutter bears against, or embeds into, the stop.

30. An aspiration biopsy system including:
a single use biopsy device according to claim 29; and
a tool including:
a tubular portion having an end that is rigidly connected to the opening of the receptacle;
a cutter driver including a hollow rod having a near end and a distal end, the cutter driver slidably received within the tubular portion so that the distal end bears against the portion of the cutter, the cutter driver being slidably movable over an extent to move the cutter towards the stop; and
a suction source in fluid communication with the interior region, the suction source operable to reduce pressure in the interior region of the receptacle to draw tissue into the interior region;
wherein over the extent of movement of the cutter driver, an exterior perimeter of the cutter driver remains sealably received within the seal to provide a hermetically sealed region between the port and the suction source when the port is in contact with the biopsy site.

31. An aspiration biopsy system, the system including:
a single use biopsy device, the device including a receptacle having a port for allowing tissue from the biopsy site to protrude into the receptacle, an interior region for containing a biopsy sample obtained by the device, a cutter supported in the receptacle and arranged so that when tissue from a biopsy site protrudes into the receptacle through the port the cutter is movable to sever the tissue so as to obtain a biopsy sample, and a stop for arresting the cutter after the cutter has severed the tissue so that the arresting of the cutter prevents reuse of the device, wherein the cutter and the stop are arranged to sever the tissue when the cutter bears against, or embeds into, the stop;
a seal positioned in the receptacle and arranged to receive a section of the cutter driver so that an outside perimeter of the cutter driver forms a sealed engagement with an inside perimeter of the seal;
a suction line connecting the interior region of the receptacle to a suction source operable to reduce pressure in the receptacle so as to thereby draw tissue into the interior region, the suction line including a cutter driver that is operable to move the cutter;
wherein the cutter driver is arranged so that an edge of the cutter abuts against an edge of the cutter driver so that the cutter is responsive to movement of the cutter driver in the direction of the stop.

32. A method of obtaining a biopsy sample from a biopsy site, including:
obtaining a single use biopsy device, the device including a receptacle having a port for allowing tissue from a biopsy site to protrude into the receptacle, an interior region for containing a biopsy sample obtained by the device, a cutter supported in the receptacle and arranged so that when tissue from a biopsy site protrudes into the receptacle through the port the cutter is movable to sever the tissue so as to obtain a biopsy sample and a stop for arresting the cutter after the cutter has severed the tissue so that the arresting of the cutter prevents reuse of the device;
placing the port of the biopsy device against the biopsy site;
operating a suction source in fluid communication with the interior region of the receptacle so as to draw tissue from the biopsy site thereinto;
operating a cutter driver to move a cutting edge of the cutter towards the stop to sever the tissue protruding into the interior region through the port to thereby obtain a biopsy sample; and
ceasing operation of the cutter driver after the cutter has been arrested by the stop by way of the cutting edge embedding into the stop.

33. A method according to claim 32 further including controllably fracturing the receptacle along at least one recess or zone of weakness of the receptacle to access the biopsy sample for removal.

34. A method according to claim 32 wherein the method is conducted to obtain a biopsy sample from the rectum of a patient.

35. A method according to claim 33 wherein the method is conducted to obtain a biopsy sample from the rectum of a patient.

36. A single use biopsy device including:
a receptacle having a port for allowing tissue from a biopsy site to protrude into the receptacle;
a cutter supported in the receptacle and arranged so that when tissue from a biopsy site protrudes into the receptacle through the port the cutter is movable to sever the tissue so as to obtain a biopsy sample; and
a stop for arresting the cutter after the cutter has severed the tissue;
wherein the arresting of the cutter by the stop prevents reuse of the device, and, wherein the cutter includes a cutting edge that is movable towards the stop over a path of movement so as to provide a severing action therebetween, the stop obstructing the path of movement and being cuttable by the blade so that the arresting of the cutter includes the cutting edge cutting into the stop to embed therein.

37. A single use biopsy device including:
a receptacle having a port for allowing tissue from a biopsy site to protrude into the receptacle;
a cutter supported in the receptacle and arranged so that when tissue from a biopsy site protrudes into the receptacle through the port the cutter is movable to sever the tissue so as to obtain a biopsy sample; and
a stop for arresting the cutter after the cutter has severed the tissue;
wherein the arresting of the cutter by the stop prevents reuse of the device, and, wherein the cutter and the stop are arranged to sever the tissue when the cutter bears against, or embeds into, the stop.

38. A device according to claim 1 wherein the receptacle includes a receiving portion for receiving a cutter driver operable to move the cutter to sever the tissue.

39. A device according to claim 27 further including:
a seal located between the opening and the internal region, the seal having an inside perimeter for sealably engaging with a cutter driver operable to move the cutter towards the stop;
wherein at least a portion of the cutter is located radially inwardly relative to the inside perimeter of the seal for access by a cutter driver having an outside perimeter of substantially the same size as the inside perimeter of the seal.

* * * * *